(12) United States Patent
Bethell et al.

(10) Patent No.: US 8,674,120 B2
(45) Date of Patent: Mar. 18, 2014

(54) PROCESS FOR MANUFACTURING ZERANOL

(75) Inventors: John Richard Bethell, Charlottetown (CA); Gary Robert Reid, Charlottetown (CA); Krista Marie Affleck, Charlottetown (CA); Tibor Breining, Charlottetown (CA)

(73) Assignee: Intervet International B.V., Boxmeer (NL)

( * ) Notice: Subject to any disclaimer, the term of this patent is extended or adjusted under 35 U.S.C. 154(b) by 379 days.

(21) Appl. No.: 13/127,392

(22) PCT Filed: Nov. 3, 2009

(86) PCT No.: PCT/EP2009/064486
§ 371 (c)(1),
(2), (4) Date: Sep. 6, 2011

(87) PCT Pub. No.: WO2010/115478
PCT Pub. Date: Oct. 14, 2010

(65) Prior Publication Data
US 2012/0016137 A1  Jan. 19, 2012

Related U.S. Application Data

(60) Provisional application No. 61/168,011, filed on Apr. 9, 2009.

(51) Int. Cl.
*C07D 493/00* (2006.01)
(52) U.S. Cl.
USPC .......................................................... 549/270
(58) Field of Classification Search
USPC .......................................................... 549/270
See application file for complete search history.

(56) References Cited

U.S. PATENT DOCUMENTS

| 3,239,345 A | 3/1966 | Hodge et al. |
|---|---|---|
| 3,574,235 A | 4/1971 | Young |
| 3,687,982 A | 8/1972 | Young |
| 3,704,248 A | 11/1972 | Hodge |
| 3,704,249 A | 11/1972 | Czaja et al. |
| 3,808,233 A | 4/1974 | Hodge |
| 4,148,808 A | 4/1979 | Hodge |
| 5,136,056 A | 8/1992 | Moimas et al. |

FOREIGN PATENT DOCUMENTS

| EP | 0 332 047 | 9/1989 |
|---|---|---|
| FR | 2 668 487 | 4/1992 |
| GB | 1152677 | 5/1969 |
| GB | 1152678 | 5/1969 |

OTHER PUBLICATIONS

Hellwig et al., "Pochonins A-F, New Antiviral and Antiparasitic Resorcylic Acid Lactones from *Pochonia chlamydosporia* var. *catenulata*", Journal of Natural Products, 2003, pp. 829-837, vol. 66.
Urry et al., "The Structure of Zearalenone", Tetrahedron Letters, 1966, pp. 3019-3311, vol. 27.
Hellwig, et al., "Pochonins A-F, New Antiviral and Antiparasitic Resorcylic Acid Lactones from *Pochonia chlamydosporia* var. *Catenulata*", J. Nat. Prod., 66(6):829-837, 2003.
Urry, et al., "The Structure of Zearalenone", Tetrahedron Letters, 7(27):3109-3114, 1966.
International Search Report, in corresponding PCT/EP2009/064486, mailed Dec. 16, 2009.
The Merck Index. An Encyclopedia of Chemicals, Drugs, and Biologicals, 4th Edition, Merck & Co., Inc., 2006, pp. 1745-1746.
Sharkawy et al., "Microbial Transformation of Zearalenone. 2. Reduction, Hydroxylation, and Methylation Products", Journal of Organic Chemistry, 1988, 53: 515-519.
Smith, M. B., March's Advanced Organic Chemistry, Reactions, Mechanisms, and Structure, 6th Edition, Wiley, NY, 2007, pp. 580-582.
Snatzke, "79. Preparation via Diastereoselective Hydrogenation, Absolute Conformation and Configuration of Exogeneous Anabolic Zeranol ((3S,7R)-3,4,5,6,7,8,9,10,11,12-Decahydro-7,14,16-trihydroxy-3-methyl-1H-2benzoxacyclotetradecin-1-one)", Helvetica Chimica Acta, 1986, 69: 734-748.
Sunjic et al., "Enzymatic Kinetic Separation of Steroisomeric Macrocyclic Lactone Derivatves, 7alpha,Beta-O-Acyl trans-Zearalenols and 7alpha,Beta-O-Acyl Zearanols", Tetrahedron, 1992, 48(31): 6511-6520.
Sunjic et al., "Steroselective reduction of two zeranole precursors by Bakers' yeast", Enzyme Microb. Technol., 1991, 13: 344-348.

*Primary Examiner* — Nizal Chandrakumar

(57) ABSTRACT

This invention is directed generally to a process for producing Zeranol that eliminates high pressure and high temperature hydrogenations and provides high selectivity for Zeranol at improved yields.

3 Claims, No Drawings

PROCESS FOR MANUFACTURING ZERANOL

RELATED APPLICATIONS

This application is a national stage entry under 35 U.S.C. §371 of PCT/EP2009/064486 filed on Nov. 3, 2009, which claims priority to U.S. Provisional Application No. 61/168,011 filed on Apr. 9, 2009.

FIELD OF THE INVENTION

This invention relates to a new and novel process for producing Zeranol of Formula I, (CAS Name: (3S,7R)-3,4,5,6,7,8,9,10,11,12-decahydro-7,14,16-trihydroxy-3-methyl-1H-2-benzoxacyclotetradecin-1-one, CAS Number: 26538-44-3), an anabolic agent that promotes weight gain in cattle. The present process is chemically more efficient than any previously known Zeranol processes, resulting in higher yields of the desired active Zeranol compound to its inactive diastereomer Taleranol of Formula II (CAS Name: (3S,7S)-3,4,5,6,7,8,9,10,11,12-decahydro-7,14,16-trihydroxy-3-methyl-1H-2-benzoxacyclotetradecin-1-one, CAS Number: 42422-68-4). It also eliminates the hazards of previously known processes that required high pressure hydrogen.

BACKGROUND OF THE INVENTION

Zeranol is an anabolic agent of Formula I. It is widely used in veterinary medicine for promoting weight gain in ruminants and other animals.

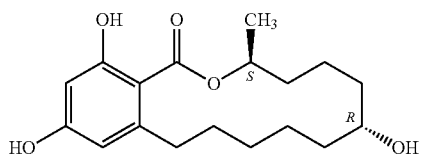

Formula I

Zeranol has been widely used to promote the growth of cattle and other domestic animals to maximize both rate of weight gain and the absolute amount of weight gain per average amount of food consumed, achieving higher feed efficiency.

Zeranol has been commercially available in a formulation known as Ralgro® (Intervet Schering-Plough Animal Health Corporation).

The first process for producing Zeranol, see Urry et al, *Tetrahedron Letters*, 1966, 27, 3109-3114, was non-specific, and was developed with a two step reduction of zearalenone using two different catalysts, and performing hydrogenation at both atmospheric pressure and elevated pressure. This route is not commercially efficient and no attempts were made to separate the resulting mixture of diastereomers.

Zeranol has been conventionally produced, see GB 1152678, using a single vessel, high pressure, high temperature hydrogenation with a Raney-nickel catalyst. Under these, conditions the ketone and alkene groups are both reduced producing both Zeranol and Taleranol. The resulting product requires multiple recrystallizations for purification and provides low recovery of the preferred Zeranol.

The process for producing Zeranol typically starts with Zearalenone of Formula III (CAS Name: (3S,11E)-3,4,5,6,9,10-hexahydro-14,16-dihydroxy-3-methyl-1H-2-benzoxacyclotetradecin-1,7(8H)-dione, CAS Number: 17924-92-4).

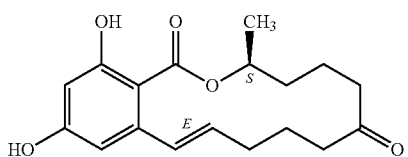

Formula III

Reduction of the Zearalenone double bond followed by reduction of the ketone gives an equal mixture of the diastereomeric alcohols: Zeranol of Formula I and Taleranol of Formula II.

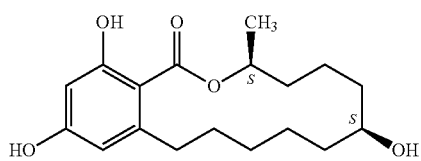

Formula II

Separation of Zeranol and Taleranol by crystallization, chromatography or other means then lead to isolation of the desired Zeranol diastereomer. See The Merck Index, 14th Ed., Merck & Co., Inc, NJ, 2006, pp 1745; Urry et al, *Tetrahedron Letters*, 1966, 27, 3109-3114 and U.S. Pat. No. 3,239,345.

Great Britain Patent 1,152,677 teaches high pressure hydrogenation of Zearalenone with Raney Nickel to afford a mixture of Zeranol and Taleranol. Multiple crystallizations in water and water/IPA mixtures are then required to provide a low yield of Zeranol. This process is inefficient in yield and requires the use of hydrogen at high pressure.

U.S. Pat. No. 3,574,235 teaches a method for separation of the Zeranol and Taleranol diastereomers resulting from the reduction of Zearalenone. This method involves selective crystallization of the undesired Taleranol, followed by dilution and crystallization of the desired Zeranol, then a second crystallization. The yields are poor and the process laborious.

U.S. Pat. No. 3,687,982 teaches a method for reducing Zearalenone to an about 55:45 mixture of the Zeranol and Taleranol diastereomers with Raney Nickel. Separation of Zeranol from Taleranol is achieved by esterification of the aliphatic hydroxyl group, selective crystallization and de-esterification. This multi-step process demonstrates little diastereomeric reduction selectivity and achieves a poor overall Zeranol yield.

U.S. Pat. No. 3,704,248 teaches a method for selective reduction of zearalenone to a mixture of diasteriomers, of which 70% is the lower melting diastereomer, and a reference method for purifying this diastereomer. The low melting diastereomer is less active than the higher melting isomer. This method is not useful for producing the higher melting diastereomer.

U.S. Pat. No. 3,704,249 teaches the selective reduction of Zearalenone or Zearalanone of Formula IV (CAS Name: (3S)-3,4,5,6,9,10,11,12-octahydro-14,16-dihydroxy-3-methyl-1H-2-benzoxacyclotetradecin-1,7(8H)-dione, CAS Number: 5975-78-0)

Formula IV with a variety of reducing agents, including aluminum alkoxides. The preferred method is to reduce the 2,4 diethers of Zearalenone or Zearalanone with aluminum tri-t-butoxide. No yields are reported. Selectivity is not defined.

U.S. Pat. No. 3,808,233 teaches a method of selective reduction of zearalenone preferentially to the more active diastereomer of Zeranol, by hydrogenation at 50 psi with a platinum catalyst in the presence of a weak acid. Selectivities of about 75:25 are noted, but no results above that selectivity are reported and the hydrogenation required elevated pressures.

U.S. Pat. No. 4,148,808 teaches a method for reduction of Zearalenone with Raney nickel in isopropanol, followed by introduction of hydrogen and further reduction of the double bond. This patent discusses the concept of slow distillation of solvent to enhance selectivity, but the best enhancement provides only a 65:35 Zeranol to Taleranol selectivity that is contaminated with unreacted Zearalanone.

Snatzke et al. reported a method for diastereoselective reduction of the dibenzylderivative of zearalenone with a chiral borane complex, followed by separation of the diastereomers by chromatography and further hydrogenation with Raney nickel. The starting material must be prepared from zearalenone in an extra synthetic step. The chiral borane complex is prepared in a multistep process. This multi-step process is not as efficient as a more direct process. (*PECS Int. Conf. Chem. Biotechnol. Biol. Act. Nat. Prod.* [Prod] $3^{rd}$ (1987), Meeting Date 1985, 4, 294-298). More detail is provided in Helv. Chim. Acta, 1986, 69, 734-748, and additional chiral boranes are described, but the process suffers from the limitations noted above.

Sharkawy and Abul-Hajj (*J. Org. Chem.* 1988, 515-519) describe a process for microbial reduction of zearalenone to Zeranol in 20% yield.

EU 332047 (a published patent application) discloses a method for separating the diastereomers of Zeranol by crystallization from acetonitrile.

French Patent 2,668,487, teaches an economical process to reduce zearalenone to Zeranol using hydrogen and a nickel-aluminum catalyst. It results in a 50:50 mixture of diastereomers that must be separated through further crystallization.

Sunjic et al., *Enzyme Microb. Technol.*, 1991, 13, 344-348, report the reduction of Zearalenone and Zearalanone to mixtures of Zeranol and Taleranol with some selectivity, but in low yield. This process is not practical at an industrial scale because of poor yields and the need to separate the diastereomers after reduction.

U.S. Pat. No. 5,136,056 teaches a process for catalytic reduction of Zearalenone with Raney nickel followed by double recrystallization of the mixture of Zeranol and Taleranol diastereomers. Mother liquors of each recrystallization are recycled, sometimes with additional chemical steps, to provide an overall high throughput of material to the desired Zeranol.

Sunjic (*Tetrahedron*, 1992, 48, 6511-6520) reports a method for separation of the acyl esters of the diastereomeric mixture of Zeranol by enzymatic kinetic separation using lipases.

In view of the prior art described above, the present invention teaches a new and novel process for manufacturing Zeranol that provides an almost three fold increase in yield and selectivity to Zeranol of 85:15 to Taleranol. The invention teaches a safe, economical and efficient process for commercial manufacture of Zeranol.

SUMMARY OF THE INVENTION

One object of the present invention is to obtain a process for producing a compound of Formula V:

Formula V wherein:

$R_1$ and $R_2$ are independently hydrogen, $C_{1-6}$ alkyl, $C_{3-8}$ cycloalkyl, $C_{2-6}$ alkenyl, $C_{2-6}$ alkynyl, $C_{1-6}$ aralkyl, $C_{2-6}$ aralkenyl, $C_{3-6}$ heterocyclic, benzyl, phenyl or phenyl alkyl where the phenyl ring may be substituted by one or two halogens, one or two nitro groups, $C_{1-6}$ alkyl or $C_{1-6}$ alkoxy; $C_{1-6}$ alkylcarbonyl, $C_{3-8}$ cycloalkylcarbonyl, $C_{2-6}$ alkenylcarbonyl, $C_{2-6}$ alkenylcarbonyl, $C_{2-6}$ alkynylcarbonyl, $C_{1-6}$ alkoxycarbonyl, $C_{3-6}$ heterocyclic carbonyl, benzylcarbonyl, phenylcarbonyl, phenyl alkylcarbonyl where the phenyl ring may be substituted by one or two halogens, one or two nitro groups, $C_{1-6}$ alkyl or $C_{1-6}$ alkoxy; $C_{1-6}$ alkoxycarbonyl, $C_{3-8}$ cycloalkoxycarbonyl, benzyloxycarbonyl, phenyloxycarbonyl or phenyl alkoxycarbonyl where the phenyl ring may be substituted by one or two halogens, one or two nitro groups, $C_{1-6}$ alkyl or $C_{1-6}$ alkoxy; or an acid addition salt thereof that eliminates limitations of prior art processes and results in improved selectivity and yield of the compound of Formula V.

In some embodiments, $R_1$ and $R_2$ are each hydrogen and the compound of Formula V is Zeranol of Formula I.

The process of the invention comprises initially reducing the ketone function of a compound of Formula VI:

Formula VI wherein: $R_1$ and $R_2$ are as previously defined in a solvent in the presence of a Meerwein Ponndorf-Verley reducing agent of the formula: $Al(OR_3)_3$, wherein:

$R_3$ is $C_{1-6}$ alkyl, $C_{3-8}$ cycloalkyl, $C_{2-6}$ alkenyl, $C_{2-6}$ alkynyl, $C_{1-6}$ aralkyl, $C_{2-6}$ aralkenyl, $C_{3-6}$ heterocyclic, benzyl or phenyl.

In some embodiments, $R_1$ and $R_2$ are each hydrogen and the compound of Formula VI is Zearalenone of Formula III.

In some embodiments, the solvent is 2-propanol and $R_3$ is isopropyl such that the Meerwein Ponndorf-Verley reducing agent is aluminum isopropoxide (CAS Number 555-31-7).

The compound of Formula VI is reduced to a mixture of compounds of Formulas VII and VIII:

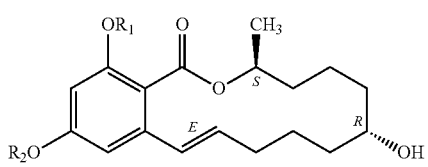

Formula VII

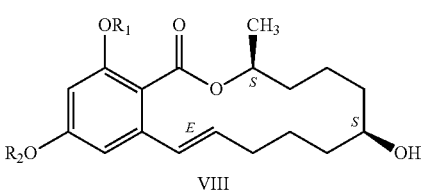

Formula VIII wherein: $R_1$ and $R_2$ are as previously defined.

In some embodiments, the ratio of the compound of Formula VII to the compound of Formula VIII is at least 60:40. In some embodiments the ratio is at least 75:25. In some particular embodiments the ratio is at least 85:15.

In some embodiments, $R_1$ and $R_2$ are each hydrogen and the compound of Formula VII is α-Zearalenol (CAS Name: (3S,7R,11E)-3,4,5,6,7,8,9,10-octahydro-7,14,16-trihydroxy-3-methyl-1H-2-benzoxacyclotetradecin-1-one, CAS Number: 36455-72-8) and the compound of Formula VIII is β-Zearalenol (CAS Name: (3S,7S,11E)-3,4,5,6,7,8,9,10-octahydro-7,14,16-trihydroxy-3-methyl-1H-2-Benzoxacyclotetradecin-1-one, CAS Number: 71030-11-0).

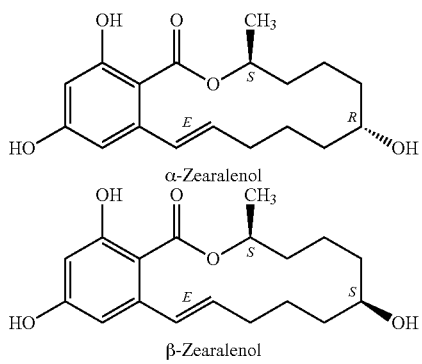

In some embodiments, the compounds of Formula VII and VIII where $R_1$ and $R_2$ are each not hydrogen are converted to α-Zearalenol and β-Zearalenol (i.e., where $R_1$ and $R_2$ are each hydrogen) by methods known to those skilled in the art. Such methods are described in: Smith, M. B.; March, J. *March's Advanced Organic Chemistry*, 6th Ed., Wiley, NY, 2007, pp 580-582, the contents of which are hereby incorporated by reference.

In some embodiments, the ratio of α-Zearalenol to β-Zearalenol is at least 60:40. In some embodiments the ratio is at least 75:25. In some particular embodiments the ratio is at least 85:15.

In some embodiments, the process of the invention further continues by quenching the reduction with an acid then exchanging the initial solvent with an alternative solvent.

In some embodiments, the reduction is quenched with 6M HCl and 2-propanol, the initial solvent, is exchanged with methanol.

In some embodiments, the process of the invention continues by reducing the double bond in the compounds of Formula VII and VIII with a reducing agent in a solvent to the compounds of Formula IX and X:

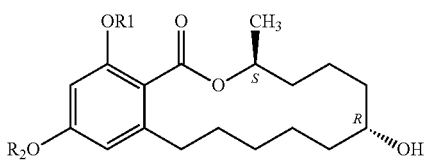

Formula IX

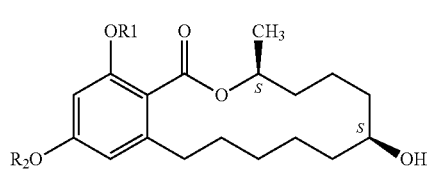

Formula X

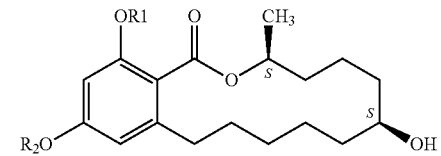

wherein $R_1$ and $R_2$ are as previously defined.

In some embodiments, the reducing agent is a catalyst and hydrogen.

In some embodiments, the catalyst is palladium or nickel and the solvent is an alcohol. In some embodiments the catalyst is palladium and the solvent is methanol.

In some embodiments, $R_1$ and $R_2$ are each hydrogen and the compound of Formula IX is Zeranol of Formula I and the compound of Formula X is Taleranol of Formula II.

In some embodiments, the compounds of Formula IX and X are converted to Zeranol and Taleranol by methods known to those skilled in the art and previously described.

In some embodiments, the ratio of the compound of Formula IX to the compound of Formula X is at least 60:40. In some embodiments the ratio is at least 75:25. In particular embodiments, the ratio is at least 85:15.

In some embodiments, the ratio of Zeranol to Taleranol is at least 60:40. In some embodiments the ratio is at least 75:25. In particular embodiments, the ratio is at least 85:15.

In some embodiments, the process of the invention continues by precipitating the compounds of Formulas IX and X. In some embodiments, the precipitation is performed by water addition.

In some embodiments, the at least 60:40 ratio of compound of Formula IX to the compound of Formula X is precipitated by addition of water to the methanol solvent. In some embodiments, the at least 75:25 ratio of compound of Formula IX to the compound of Formula X is precipitated by addition of water to the methanol solvent. In some embodiments, the at least 85:15 ratio of compound of Formula IX to the compound of Formula X is precipitated by addition of water to the methanol solvent.

In some embodiments, the at least 60:40 ratio of Zeranol to Taleranol is precipitated by addition of water to the methanol solvent.

In some embodiments, the at least 75:25 ratio of Zeranol to Taleranol is precipitated by addition of water to the methanol solvent.

In some embodiments, the at least 85:15 ratio of Zeranol to Taleranol is precipitated by addition of water to the methanol solvent.

In some embodiments, the process of the invention continues by removing unwanted impurities by washing the precipitated compounds of Formula IX and X with a hydrocarbon solvent. A non limiting list of hydrocarbon solvents include pentane, hexane, heptane, octane, their geometric isomers and mixtures thereof. In some embodiments, the hydrocarbon solvent is heptane.

In some embodiments, the precipitated at least 60:40 ratio of the compound of Formula IX to the compound of Formula X is washed with heptane to remove unwanted impurities.

In some embodiments, the at least 75:25 ratio of the compound of Formula IX to the compound of Formula X is washed with heptane to remove unwanted impurities. In some embodiments, the at least 85:15 ratio of the compound of Formula IX to the compound of Formula X is washed with heptane to remove unwanted impurities.

In some embodiments, the precipitated at least 60:40 ratio of Zeranol to Taleranol is washed with heptane to remove unwanted impurities. In some embodiments, the at least 75:25 ratio of Zeranol to Taleranol is washed with heptane to remove unwanted impurities. In some embodiments, the at least 85:15 ratio of Zeranol to Taleranol is washed with heptane to remove unwanted impurities.

In some embodiments, the process of the invention continues by reducing the amount of the compound of Formula X in the hydrocarbon washed mixture of the compounds of Formula IX and X and producing a pure compound of Formula IX.

In some embodiments, the pure compound of Formula IX is obtained by crystallization of the hydrocarbon washed mixture of the compounds of Formula IX and X from a solvent or mixture of solvents. In some embodiments the crystallization is in a methanol and water solvent system.

In some embodiments, the purification of the at least 60:40 ratio of the compound of Formula IX to the compound of Formula X is accomplished by crystallization from a methanol and water solvent system. In some embodiments, the purification of the at least 75:25 ratio of the compound of Formula IX to the compound of Formula X is accomplished by crystallization from a methanol and water solvent system. In some embodiments, the purification of the at least 85:15 ratio of the compound of Formula IX to the compound of Formula X is accomplished by crystallization from a methanol and water solvent system.

In some embodiments, the purification of the at least 60:40 ratio of Zeranol to Taleranol is accomplished by crystallization from a methanol and water solvent system. In some embodiments, the purification of the at least 75:25 ratio of Zeranol to Taleranol is accomplished by crystallization from a methanol and water solvent system. In some embodiments, the purification of the at least 85:15 ratio of Zeranol to Taleranol is accomplished by crystallization from a methanol and water solvent system.

In some embodiments, the purity of the compound of Formula IX is at least about 98%. In some embodiments the purity of the compound of Formula IX is at least about 99%. In some embodiments, the purity of the compound of Formula IX is at least about 99.5%.

In some embodiments the yield of the compound of Formula IX is at least about 40%. In some embodiments the yield of the compound of Formula IX is at least about 43%. In some embodiments the yield of the compound of Formula IX is at least about 45%.

In some embodiments, the compound of Formula IX is converted to Zeranol and by methods known to those skilled in the art and previously described.

In some embodiments, the purity of Zeranol is at least about 98%. In some embodiments the purity of Zeranol is at least about 99%. In some embodiments, the purity of Zeranol is at least about 99.5%.

In some embodiments the yield of Zeranol is at least about 40%. In some embodiments the yield of Zeranol is at least about 43%. In some embodiments the yield of Zeranol is at least about 45%.

DETAILED DESCRIPTION OF THE INVENTION

When used herein and in the appended claims, the terms listed below, unless otherwise indicated, will be used and are intended to be defined as indicated immediately below. Definitions for other terms can occur throughout the specification. It is intended that all terms used include the plural, active tense and past tense forms of a term.

The term "alkyl" means a saturated straight or branched alkyl such as methyl, ethyl, propyl, or sec-butyl. Alternatively, the number of carbons in an alkyl can be specified. For example, "$C_{1-6}$ alkyl" means an "alkyl" as described above containing 1, 2, 3, 4, 5 or 6 carbon atoms.

The term "$C_{3-8}$ cycloalkyl" means a saturated cyclic hydrocarbon group (i.e., a cyclized alkyl group) containing 3, 4, 5, 6, 7 or 8 carbon atoms. Example cycloalkyl groups include, without limitation, cyclopropyl, cyclobutyl, cyclopentyl, cyclohexyl and the like.

The term "$C_{2-6}$ alkenyl" means an unsaturated branched or unbranched hydrocarbon group having at least one double carbon-carbon (—C═C—) bond and containing 2, 3, 4, 5, or 6 carbon atoms. Example alkenyl groups include, without limitation, ethenyl, 1-propenyl, isopropenyl, 2-butenyl, 1,3-butadienyl, 3-pentenyl and 2-hexenyl, and the like.

The term "$C_{2-6}$ alkynyl" means an unsaturated branched or unbranched hydrocarbon group having at least one triple carbon-carbon (—C≡C—) bond and containing 2, 3, 4, 5, or 6 carbon atoms. Example alkynyl groups include, without limitation, ethynyl, 1-propynyl, 2-propynyl, 2-butynyl, 3-butynyl, 2-penten-4-nyl, and the like.

The term "$C_{1-6}$ aralkyl" means a $C_{1-6}$ alkyl as defined herein substituted by an aryl group that is any radical derived from an aromatic hydrocarbon by the removal of a hydrogen atom.

The term "$C_{2-6}$ aralkenyl" means a $C_{2-6}$ alkenyl as defined herein substituted by an aryl group that is any radical derived from an aromatic hydrocarbon by the removal of a hydrogen atom.

The term "$C_{3-6}$ heterocyclic group" means a ring system radical where one or more of the ring-forming carbon atoms is replaced by a heteroatom, such as an oxygen, nitrogen, or sulfur atom, which include mono- or polycyclic (e.g., having 2 or more fused rings) ring systems as well as spiro ing systems. The ring system can contain 3, 4, 5, or 6 carbon atoms and can be aromatic or non-aromatic.

"Benzyl" means the monovalent radical $C_6H_5CH_2$ of methylbenzene, where benzene is the aromatic hydrocarbon $C_6H_6$.

"Substituted benzyl" means benzyl substituted by $C_1$ to $C_6$ alkyl or "halo", where benzyl is the univalent radical $C_6H_5CH_2$, formally derived from toluene (i.e., methylbenzene).

"Phenyl" means the monovalent radical $C_6H_5$ of benzene, which is the aromatic hydrocarbon $C_6H_6$.

The term "phenyl alkyl" means an alkyl as defined herein substituted by phenyl as defined herein.

The term "halo" or "halogen" means fluoro, chloro, bromo or iodo.

The term "nitro" means a —NO₂ radical.

The term "C$_{1-6}$ alkoxy" means an alkyl-O— group, where the term "alkyl" is defined herein. Example alkoxy groups include, without limitation, methoxy, ethoxy, propoxy (e.g., n-propoxy and isopropoxy), t-butoxy, and the like.

The term "C$_{1-6}$ alkylcarbonyl" means a C$_{1-6}$ alkyl as defined herein attached through a carbonyl.

The term "carbonyl" means a carbon attached to an oxygen by a double bond (C=O).

The term "C$_{3-8}$ cycloalkylcarbonyl" means a C$_{3-8}$ cycloalkyl as defined herein attached through a carbonyl.

The term "C$_{2-6}$ alkenylcarbonyl" means a C$_{2-6}$ alkenyl as defined herein attached through a carbonyl.

The term "C$_{2-6}$ alkynylcarbonyl" means a C$_{2-6}$ alkynyl as defined herein attached through a carbonyl.

The term "C$_{1-6}$ alkoxycarbonyl" means a C$_{1-6}$ alkoxy as defined herein attached through a carbonyl.

The term "C$_{3-6}$ heterocyclic carbonyl" means a C$_{3-6}$ heterocyclic group as defined herein attached through a carbonyl.

The term "benzylcarbonyl" means a benzyl as defined herein attached through a carbonyl.

The term "phenylcarbonyl" means a phenyl as defined herein attached through a carbonyl.

The term "phenyl alkylcarbonyl" means a phenyl alkyl as defined herein attached through a carbonyl.

The term "C$_{3-8}$ cycloalkoxycarbonyl" means a C$_{3-8}$ cycloalkyl as defined herein attached through the oxygen of an oxycarbonyl.

The term "oxycarbonyl" means an oxygen atom attached to a carbonyl as defined herein.

The term "benzyloxycarbonyl" means a benzyl group as defined herein attached through the oxygen of an oxycarbonyl The term "phenyloxycarbonyl" means a phenyl group as defined herein attached through the oxygen of an oxycarbonyl.

The term "phenyl alkoxycarbonyl" means a phenyl alkyl group as defined herein attached through the oxygen of an oxycarbonyl.

Throughout the specification and the appended claims, a given chemical formula or name shall encompass all pharmaceutically acceptable salts thereof and solvates thereof such as for instance hydrates.

The reactions described herein can be carried out in a suitable reaction vessel which is a container known to those of ordinary skill in the art that is capable of holding the reactants while allowing the reaction steps to proceed to completion. The size and type of vessel might, e.g., depend upon the size of the batch and the specific reactants selected.

In some embodiments, the present invention provides a process for preparing a compound of Formula V:

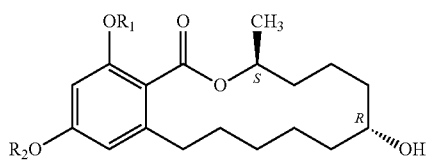

Formula V wherein:

R$_1$ and R$_2$ are independently hydrogen, C$_{1-6}$ alkyl, C$_{3-8}$ cycloalkyl, C$_{2-6}$ alkenyl, C$_{2-6}$ alkynyl, C$_{1-6}$ aralkyl, C$_{2-6}$ aralkenyl, C$_{3-6}$ heterocyclic, benzyl, substituted benzyl, phenyl or phenyl alkyl where the phenyl ring may be substituted by one or two halogens, one or two nitro groups, C$_{1-6}$ alkyl or C$_{1-6}$ alkoxy; C$_{1-6}$ alkylcarbonyl, C$_{3-8}$ cycloalkylcarbonyl, C$_{2-6}$ alkenylcarbonyl, C$_{2-6}$ alkynylcarbonyl, C$_{1-6}$ alkoxycarbonyl, C$_{3-6}$ heterocyclic carbonyl, benzylcarbonyl, phenylcarbonyl, phenyl alkylcarbonyl where the phenyl ring may be substituted by one or two halogens, one or two nitro groups, C$_{1-6}$ alkyl or C$_{1-6}$ alkoxy; C$_{3-8}$ cycloalkoxycarbonyl, benzyloxycarbonyl, phenyloxycarbonyl or phenyl alkoxycarbonyl where the phenyl ring may be substituted by one or two halogens, one or two nitro groups, C$_{1-6}$ alkyl or C$_{1-6}$ alkoxy; or an acid addition salt thereof.

In some embodiments, R$_1$ and R$_2$ are each hydrogen and the compound of Formula V is Zeranol. Zeranol is a compound used in veterinary medicine to promote weight gain in ruminants and other animals.

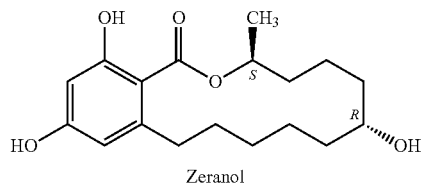

Zeranol

In some embodiments, the process of the invention comprises initially reducing the ketone function of a compound of Formula VI:

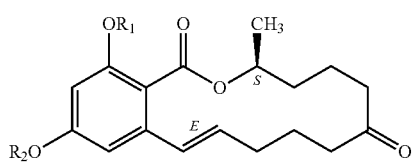

Formula VI wherein R$_1$ and R$_2$ are as previously defined in a solvent such as but not limited to acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof;

in the presence of a Meerwein Ponndorf-Verley reducing agent of the formula: Al(OR$_3$)$_3$ wherein:

R$_3$ is C$_{1-6}$ alkyl, C$_{3-8}$ cycloalkyl, C$_{2-6}$ alkenyl, C$_{2-6}$ alkynyl, C$_{1-6}$ aralkyl, C$_{2-6}$ aralkenyl, C$_{3-6}$ heterocyclic, benzyl or phenyl.

In particular embodiments of the invention, R$_1$ and R$_2$ are each hydrogen and the compound of Formula VI is Zearalenone.

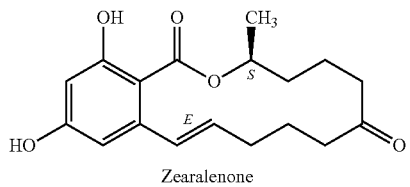
Zearalenone

In particular embodiments of the invention, the solvent is 2-propanol.

In particular embodiments of the invention, $R_3$ is isopropyl and the reducing agent is aluminum isopropoxide (CAS Number 555-31-7).

The weight to weight ratio of solvent to the compound of Formula VI can range from about 5 to 1 up to about 15 to 1. In particular embodiments of the invention, the weight to weight ratio of isopropanol to Zearalenone is between about 8 to 1 and about 12 to 1. In some embodiments, the ratio is between about 10 and 11 to 1.

The weight to weight ratio of the Meerwein Ponndorf-Verley reducing agent to the compound of Formula VI can range from about 1 to 1 up to about 5 to 1. In particular embodiments of the invention, the Meerwein Ponndorf-Verley reducing agent is aluminum isopropoxide and the ratio of aluminum isopropoxide to Zearalenone is between about 3 and 4 to 1.

The temperature of the reduction can range from about 60° C. up to the boiling point of the solvent. The pressure can range from about atmospheric pressure up to about 30 psi. In particular embodiments, the temperature of the isopropanol solvent is about 75° C. and the reaction pressure ranges from about 5 to 10 psi.

The compound of Formula VI is reduced to a mixture of compounds of Formula VII and VIII:

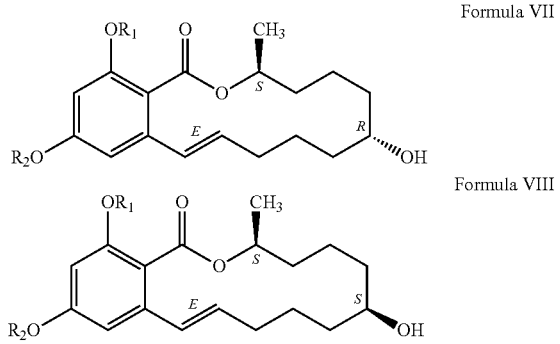

wherein:

$R_1$ and $R_2$ are as previously defined.

The Meerwein Ponndorf-Verley reduction of the compound of Formula VI continues until the ratio of the product compound of Formula VII to the compound of Formula VIII is at least about 60 to 40, more preferably 75:25, and most preferably 85:15.

In some embodiments, $R_1$ and $R_2$ are each hydrogen and the compound of Formula VII is α-Zearalenol (CAS Name: (3S,7R,11E)-3,4,5,6,7,8,9,10-octahydro-7,14,16-trihydroxy-3-methyl-1H-2-benzoxacyclotetradecin-1-one, CAS Number: 36455-72-8) and the compound of Formula VIII is β-Zearalenol (CAS Name: (3S,7S,11E)-3,4,5,6,7,8,9,10-octahydro-7,14,16-trihydroxy-3-methyl-1H-2-benzoxacyclotetradecin-1-one, CAS Number: 71030-11-0).

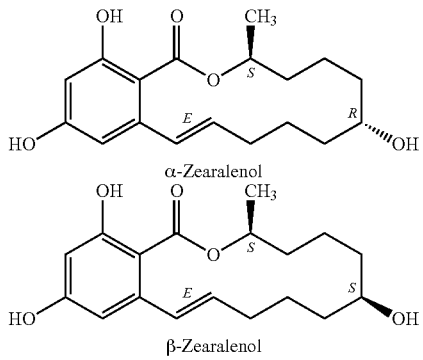
α-Zearalenol

β-Zearalenol

In some embodiments, the Meerwein Ponndorf-Verley reduction of Zearalenone continues until the ratio of α-Zearalenol to β-Zearalenol is at least 60:40, more preferably 75:25, and most preferably 85:15.

In some embodiments, the compounds of Formula VII and VIII, where $R_1$ and $R_2$ are each not hydrogen, are converted to α-Zearalenol and β-Zearalenol (i.e., where $R_1$ and $R_2$ are each hydrogen) by methods known to those skilled in the art. Such methods are described in: Smith, M. B.; March, J. *March's Advanced Organic Chemistry*, 6th Ed., Wiley, NY, 2007, pp 580-582, the contents of which are hereby incorporated by reference.

In some embodiments, the process of the invention further continues by reducing the solvent volume by distillation, cooling to ambient temperature, adding water and an acid to quench the reaction.

In some embodiments, the isopropanol is reduced to a minimal volume by distillation then cooled to ambient temperature.

In some embodiments, the isopropanol is reduced to between about 700 to 900 L and cooled to ambient temperature.

In some embodiments, about 4 weight volumes of water relative to the compound of Formula III is then added.

In some embodiments, the acid added can be an inorganic acid, an organic acid and/or a mixture thereof. A non-limiting list of suitable inorganic acids includes hydrochloric acid, sulfuric acid, nitric acid, phosphoric acid, etc. and mixtures thereof. Similarly, suitable organic acids include, for example, acetic acid, trifluoroacetic acid, methanesulfonic acid, p-toluenesulfonic acid, etc. and mixtures thereof. In a preferred aspect of the invention, the acid is hydrochloric acid.

In some embodiments, about 5.5 weight volumes relative to the compound of Formula III of 6M HCl is added ensuring that the temperature remains below about 40° C.

In some embodiments, the process of the invention continues by adding a solvent to induce an organic and aqueous phase such that the aqueous phase can be separated.

In some embodiments, the solvent is ethyl acetate.

In some embodiments, about 8 to 9 weight volumes relative to the compound of Formula III of ethyl acetate is added and the lower aqueous layer removed. The ethyl acetate layer is then washed with additional water.

In some embodiments, the ethyl acetate layer is washed three times with water

In some embodiments, the process of the invention further continues by exchanging the ethyl acetate solvent for methanol. In some embodiments, the exchange is achieved by distilling the ethyl acetate and replacing it with methanol In some embodiments, the process of the invention continues by reducing the double bond in the compounds of Formula VII and VIII with a palladium or nickel catalyst and hydrogen to the compounds of Formula IX and X:

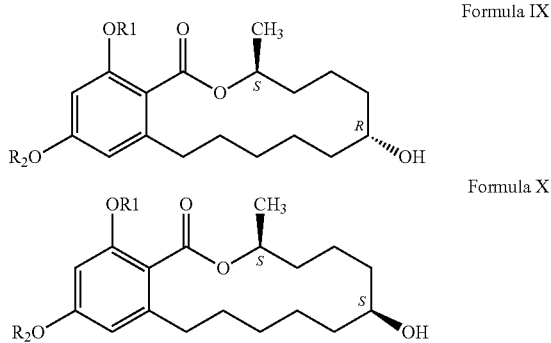

In some embodiments, the catalyst is palladium.

In some embodiments, $R_1$ and $R_2$ are each hydrogen and the compound of Formula IX is Zeranol and the compound of Formula X is Taleranol. In some embodiments, the ratio of Zeranol to Taleranol is at least 60:40, more preferably at least 75:25, and most preferably at least 85:15.

In some embodiments, the process of the invention continues by precipitating the Zeranol and Taleranol mixture by addition of water.

In some embodiments, the process of the invention continues by removing unwanted impurities by washing the precipitated Zeranol and Taleranol mixture with a hydrocarbon solvent. A non limiting list of hydrocarbon solvents include pentane, hexane, heptane, octane, their geometric isomers and mixtures thereof. In some embodiments, the hydrocarbon solvent is heptane.

In some embodiments, the purification of the desired Zeranol and elimination of the undesired Taleranol is performed by crystallization from a solvent such as but not limited to acetone, acetonitrile, 1-butanol, 2-butanol, butyl acetate, carbon tetrachloride, chlorobenzene, chloroform, cyclohexane, 1,2-dichloroethane, 1,2-dichloroethene, dichloromethane, 1,2-dimethoxyethane, N,N-dimethylacetamide, N,N-dimethylformamide, dimethylsulfoxide, 1,4-dioxane, ethanol, 2-ethoxyethanol, ethylene glycol, ethyl acetate, ethyl ether, ethyl formate, formamide, heptane, hexane, isobutyl acetate, isopropyl acetate, methyl acetate, methylethyl ketone, methanol, 2-methoxyethanol, methylbutyl ketone, methylcyclohexane, N-methylpyrrolidone, propanol, 2-propanol, tetralin, tetrahydrofuran, toluene, xylene, glycerin, water, and mixtures thereof. In some embodiments, the Zeranol purification is performed in a mixture of methanol and water. In some embodiments, the purity of Zeranol is at least 98%, preferably at least 99% and most preferably at least 99.5%. In some embodiments the yield of Zeranol is at least about 40%, preferably at least 45% and most preferably at least 50%.

In one embodiment, the process of the invention is depicted in Scheme 1.

Scheme I

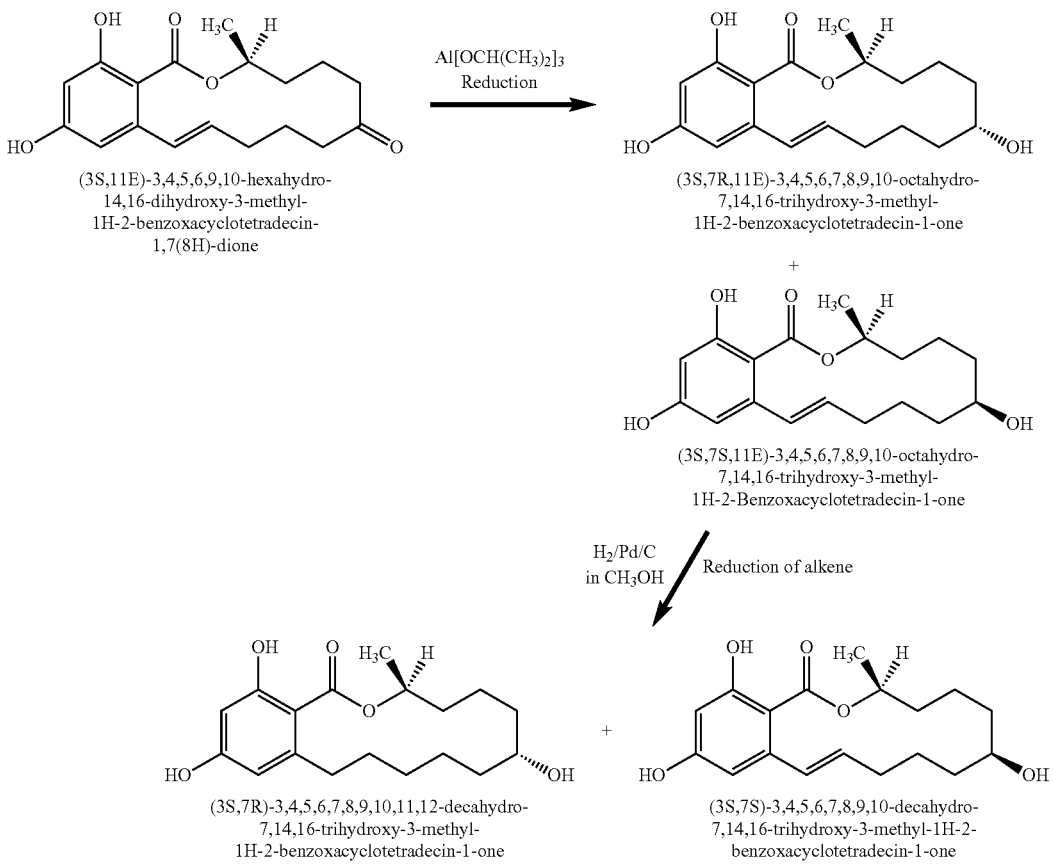

Example 1

Aluminum isopropoxide (300 g, 1.4688 moles) is added to a solution of Zearalenone (100 g, 0.3141 moles) in 1000 g (1270 mL) of 2-propanol. The mixture is stirred at 75° C. for 24 hours then the mixture is distilled to a volume of about 500 mL, cooled to ambient room temperature, 400 mL of water and 550 mL of 6N HCl are added ensuring that the reaction temperature is maintained below 40° C. The reaction is cooled to ambient room temperature and 886 g (990 mL) of ethyl acetate is added. The aqueous layer is separated and the ethyl acetate layer is extracted 2×325 mL with water and 1×325 mL with brine. The ethyl acetate is replaced with methanol by distilling off the ethyl acetate and replacing it with 380 g (480 mL) of methanol. The methanol mixture is filtered to remove insoluble matter and 10% Palladium on carbon (10 g) is added followed by hydrogen (1 atmosphere of pressure) at ambient room temperature. The reaction is stirred for 8 hours then Celite (20 g) is added and the reaction stirred for an additional hour. The reaction mixture is filtered to remove insoluble matter and water (725 mL) is added. The mixture is stirred at ambient room temperature for 4 hours during which time solid precipitate. The solids are isolated by filtration and washed with heptane (1000 mL). The solids are dissolved in methanol (890 mL) and water (470 mL) is added at ambient room temperature and solids begin to crystallize from solution. The mixture is stirred for an additional 4 hours and the solids are isolated by filtration, dried under vacuum to a moisture content of less than 0.5% to yield pure Zeranol (45.6 g, 45%).

The words "comprise", "comprises", or "comprising" in this patent (including the claims) are to be interpreted inclusively rather than exclusively.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A method for the manufacture of zearalenol comprising dissolving the zearalenone in isopropanol; forming an isopropanol solution of zearalenone; combining the isopropanol solution of zearalenone with aluminum isopropoxide to form a reaction mixture; and heating the reaction mixture to reduce the zearalenone to zearalenol.

2. The method of claim 1, wherein the zearalenol is reduced, comprising: extracting the zearalenol from the reaction mixture with ethyl acetate; and reacting the extracted zearalenol with low pressure hydrogen in methanol in the presence of a palladium catalyst to form zeranol.

3. The method of claim 1, wherein the overall yield of zeranol is at least 40% based on the zearalenone originally provided.

* * * * *